United States Patent
Patel et al.

(10) Patent No.: US 8,992,899 B2
(45) Date of Patent: *Mar. 31, 2015

(54) CLEAN VOLUME MASCARA COMPOSITIONS COMPRISING AT LEAST ONE FILM FORMER AND AT LEAST ONE SILICONE ELASTOMER

(71) Applicant: L'Oreal, Paris (FR)

(72) Inventors: Kavita Patel, East Windsor, NJ (US); Angeles Fonolla-Moreno, Westfield, NJ (US); Naoto Sugimoto, Tokyo (JP)

(73) Assignee: L'Oreal, Paris (FR)

( * ) Notice: Subject to any disclaimer, the term of this patent is extended or adjusted under 35 U.S.C. 154(b) by 21 days.

This patent is subject to a terminal disclaimer.

(21) Appl. No.: 13/731,286

(22) Filed: Dec. 31, 2012

(65) Prior Publication Data

US 2014/0186282 A1  Jul. 3, 2014

(51) Int. Cl.
| | | |
|---|---|---|
| *A61Q 1/10* | (2006.01) |
| *A61K 8/81* | (2006.01) |
| *A61K 8/891* | (2006.01) |
| *A61K 8/895* | (2006.01) |

(52) U.S. Cl.
CPC . *A61Q 1/10* (2013.01); *A61K 8/891* (2013.01); *A61K 8/895* (2013.01); *A61K 8/8152* (2013.01)
USPC ...... 424/70.7; 424/63; 424/70.12; 424/70.15; 424/70.16; 424/70.22; 424/70.31; 424/401; 424/486; 424/487

(58) Field of Classification Search
CPC ....... A61K 8/8152; A61K 8/89; A61K 8/894; A61K 8/922; A61K 2800/5424; A61K 2800/5426; A61K 2800/594; A61Q 1/10
USPC ........ 424/70.12, 70.122, 70.15, 70.16, 70.22, 424/70.31, 401, 486, 487
See application file for complete search history.

(56) References Cited

U.S. PATENT DOCUMENTS

| | | | |
|---|---|---|---|
| 3,937,811 A | 2/1976 | Papantoniou et al. | |
| 4,887,622 A | 12/1989 | Gueret | |
| 6,274,131 B1 * | 8/2001 | Piot et al. | 424/70.7 |
| 6,328,495 B1 | 12/2001 | Gueret | |
| 6,386,781 B1 | 5/2002 | Gueret | |
| 6,475,500 B2 * | 11/2002 | Vatter et al. | 424/401 |
| 6,581,610 B1 | 6/2003 | Gueret | |
| 6,692,173 B2 | 2/2004 | Gueret | |
| 2003/0091522 A1 | 5/2003 | Collins et al. | |
| 2003/0108498 A1 | 6/2003 | Stephens et al. | |
| 2004/0170586 A1 | 9/2004 | Ferrari et al. | |
| 2010/0196292 A1 | 8/2010 | Carson et al. | |
| 2012/0237463 A1 | 9/2012 | Patel et al. | |
| 2013/0039874 A1 * | 2/2013 | Li et al. | 424/70.7 |
| 2013/0295035 A1 * | 11/2013 | Sugimoto et al. | 424/70.16 |

FOREIGN PATENT DOCUMENTS

| | | |
|---|---|---|
| EP | 0847752 | 6/1998 |
| FR | 2232303 | 1/1975 |
| FR | 2761959 | 10/1998 |
| FR | 2792190 | 10/2000 |
| FR | 2792618 | 10/2000 |
| FR | 2796529 | 1/2001 |

OTHER PUBLICATIONS

English language abstract for EP 0847752, Jun. 17, 1998.
English language abstract for FR2792190, Oct. 20, 2000.
International Search Report and Written Opinion for PCT/US2013/077092. Apr. 28, 2014.
English language abstract for FR 2792190. Oct. 20, 2000.

* cited by examiner

*Primary Examiner* — Jane C Oswecki
(74) *Attorney, Agent, or Firm* — The Marbury Law Group, PLLC

(57) ABSTRACT

Disclosed herein are cosmetic compositions comprising at least one film-forming polymer, at least one silicone elastomer blend, and at least one wax. Also disclosed herein are methods for making up and/or enhancing the appearance of a keratinous substrate comprising applying said composition to the keratinous substrate.

19 Claims, No Drawings

CLEAN VOLUME MASCARA COMPOSITIONS COMPRISING AT LEAST ONE FILM FORMER AND AT LEAST ONE SILICONE ELASTOMER

FIELD OF THE DISCLOSURE

The disclosure relates to cosmetic compositions comprising (1) at least one film-forming polymer, (2) at least one silicone elastomer blend, and (3) at least one wax. Cosmetic compositions according to various embodiments of the disclosure may have one or more improved properties, such as improved thickening, lengthening, and/or curling of the eyelashes, improved lash separation, improved resistance to clumping and/or smudging, and/or improved ease of removal. The disclosure further relates to methods for making up and/or enhancing the appearance of a keratinous substrate, such as the eyelashes, comprising applying said composition to the keratinous substrate.

BACKGROUND

Mascara compositions are known and used in the cosmetic field to impart thickness, color, and/or length to the eyelashes. Several different mascaras have been developed in the art using various cosmetic ingredients depending on the desired cosmetic properties. For instance, it is known in the art that inclusion of one or more film formers in a mascara composition can improve various properties, such as the ability of the composition to thicken the eyelashes. It is also known, for example, that inclusion of fibers may enhance the lengthening properties of a mascara composition.

However, there still exists a need in the cosmetic art for "clean volume" mascara compositions, e.g., compositions that lengthen and separate the lashes while also volumizing or thickening the lashes without clumping. As such, there is a continuous need to invent novel cosmetic compositions which demonstrate one or more of the above-mentioned improved properties. It has now been surprisingly discovered that by incorporating (1) at least one film-forming polymer, (2) at least one silicone elastomer blend, and (3) at least one wax into a cosmetic composition, cosmetic properties such as improved thickening, lengthening, and/or curling of the eyelashes, improved lash separation, improved resistance to clumping and/or smudging, and/or improved ease of removal, can be achieved.

DESCRIPTION OF EXEMPLARY EMBODIMENTS

The disclosure relates, in various embodiments, to cosmetic compositions comprising (1) at least one film-forming polymer, present in an amount greater than or equal to about 20% by weight, relative to the total weight of the composition, (2) at least one silicone elastomer blend comprising at least one silicone cross-polymer dispersed in at least one oil, present in an amount greater than or equal to about 2% by weight, relative to the total weight of the composition, and (3) at least one wax, present in an amount greater than or equal to about 4% by weight, relative to the total weight of the composition.

One embodiment of the disclosure relates to cosmetic compositions comprising (1) at least one-film forming polymer chosen from a styrene/acrylates/ammoumium methacrylate copolymer, (2) at least one silicone elastomer blend chosen from silicone cross-polymers dispersed in dimethicone, and (3) at least one wax. In one exemplary embodiment, the film-forming polymer may, by way of example, be styrene/acrylates/ammoumium methacrylate copolymer (and) sodium lauryl sulfate (and) carylyl glycol, such as, for example, SYNTRAN 5760 CG from Interpolymer. In various exemplary embodiments, the at least one silicone elastomer blend may be chosen from dimethicone/vinyl dimethicone cross-polymer dispersed in dimethicone, such as, for example, KSG-16 from Shin-Etsu. In various exemplary embodiments, the at least one wax may be chosen from carnauba wax, beeswax, paraffin, and jojoba butter. The above-mentioned compounds may be present in the cosmetic composition in any amounts described herein as suitable for the various respective components.

Film-Forming Polymers

As used herein, the terms "film-forming polymer," "film former" and variations thereof mean a polymer capable of, by itself or in the presence of an auxiliary film-forming agent, forming a continuous film that adheres to a support and especially to keratin materials, for instance the eyelashes.

Among the film-forming polymers that may be used in the cosmetic composition disclosed herein, mention may be made of synthetic polymers, of the free-radical type or of the polycondensate type, polymers of natural origin, and mixtures thereof. For example, the film-forming polymers may be selected from vinyl (co)polymers, (meth)acrylic (co)polymers, urethane (co)polymers, and mixtures thereof. According to various embodiments, the at least one film-forming polymer is a styrene/acrylates/ammoumium methacrylate copolymer.

The film-forming polymers of the free-radical type may be chosen, for example, from vinyl polymers or copolymers, such as acrylic polymers. The vinyl film-forming polymers can result from the polymerization of monomers comprising at least one ethylenic unsaturation and at least one acidic group and/or esters of these acidic monomers and/or amides of these acidic monomers.

Monomers comprising at least one acidic group which may be used include, for example, α,β-ethylenic unsaturated carboxylic acids such as acrylic acid, methacrylic acid, crotonic acid, maleic acid or itaconic acid. In at least one embodiment, the monomers are chosen from (meth)acrylic acid and crotonic acid.

The esters of acidic monomers may be chosen, for example, from (meth)acrylic acid esters (also known as (meth)acrylates), such as (meth)acrylates of an alkyl, for example, a $C_1$-$C_{30}$ alkyl, such as a $C_1$-$C_{20}$ alkyl, (meth)acrylates of an aryl, such as a $C_6$-$C_{10}$ aryl, and (meth)acrylates of a hydroxyalkyl, such as a $C_2$-$C_6$ hydroxyalkyl.

Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate. The hydroxyalkyl (meth)acrylates may include, but are not limited to, hydroxyethyl acrylate, 2-hydroxypropyl acrylate, hydroxyethyl methacrylate and 2-hydroxypropyl methacrylate. By way of non-limiting example, the aryl (meth)acrylates may be chosen from benzyl acrylate and phenyl acrylate. The (meth)acrylic acid esters that may be used include, for example, alkyl (meth)acrylates. As disclosed herein, the alkyl group of the esters may be either fluorinated or perfluorinated, i.e., some or all of the hydrogen atoms of the alkyl group are substituted with fluorine atoms.

Examples of amides of the acid monomers include, but are not limited to, (meth)acrylamides, such as N-alkyl(meth) acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above. Examples of vinyl esters that may be mentioned include vinyl acetate, vinyl neodecanoate, vinyl pivalate, vinyl benzoate and vinyl t-butylbenzoate. Styrene monomers that may be mentioned include, but are not limited to, styrene and α-methylstyrene.

Film-forming polycondensates useful according to the instant disclosure may include, for example, polyurethanes, polyesters, polyesteramides, polyamides, epoxyester resins and polyureas. The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof. The polyesters may be obtained, in a known manner, for example by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used may, for example, be chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, such as by polycondensation of diacids with diamines or amino alcohols. Diamines that may be used include, for example, ethylenediamine, hexamethylenediamine and meta- or para-phenylenediamine. An amino alcohol that may be used is, for instance, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used. The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an —$SO_3M$ group, mention may be made, for example, of sulfoisophthalic acid, sulfoterephthalic acid, sulfophthalic acid, 4-sulfonaphthalene-2,7-dicarboxylic acid.

The copolymers used may be, for example, those based on isophthalate/sulfoisophthalate, such as copolymers obtained by condensation of diethylene glycol, cyclohexanedimethanol, isophthalic acid and sulfoisophthalic acid.

According to one embodiment of the present disclosure, the film-forming polymer may be a liposoluble polymer. Examples of suitable liposoluble polymers that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an α-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be, for example, of the vinylic type or of the allylic or methallylic type, such as tetraallyloxyethane, divinylbenzene, divinyl octanedioate, divinyl dodecanedioate and divinyl octadecanedioate.

Non-limiting examples of these copolymers which may be mentioned include: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of the liposoluble film-forming polymers which may also be mentioned include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms. Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate.

The liposoluble copolymers defined above are described, for example, in French Patent Application Publication No. 2 232 303, incorporated herein by reference in its entirety. They may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) such as copolymers of vinylpyrrolidone and of $C_2$-$C_{40}$ alkene such as $C_3$-$C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

In various embodiments, the film-forming polymer may have a Tg (glass transition temperature) value of less than 50° C. In other embodiments, the cosmetic composition of the instant disclosure comprises at least one film-forming polymer in the form of particles dispersed in an aqueous phase, which is generally known in the cosmetic art as a latex.

Commercially available aqueous dispersions of film-forming polymers which may be used are the acrylic dispersions sold under the names "Neocryl XK-90®", "Neocryl A-1070®", "Neocryl A-1090®", "Neocryl BT-62®", "Neocryl A-1079®" and "Neocryl A-523®" by the company Avecia-Neoresins, "Dow Latex 432®" by the company Dow Chemical, "Daitosol 5000 ADC)" or "Daitosol 5000 SJ" by the company Daito Kasey Kogyo; "Syntran 5760" or "Syntran 5760 CG" by the company Interpolymer or the aqueous dispersions of polyurethane sold under the names "Neorez R-981®" and "Neorez R-974®" by the company Avecia-Neoresins, "Avalure UR-405®", "Avalure UR-410®", "Avalure UR-425®", "Avalure UR-450®", "Sancure 875®", "Sancure 861®", "Sancure 878®" and "Sancure 2060®" by the company Goodrich, "Impranil 85®" by the company Bayer and "Aquamere H-1511®" by the company Hydromer; vinyl dispersions, for instance "Mexomer PAM" and also acrylic dispersions in isododecane, for instance "Mexomer PAP" by the company Chimex.

The at least one film-forming polymer may be present in the cosmetic composition in an amount greater than or equal to about 20% by weight, relative to the total weight of the cosmetic composition. In certain embodiments, the at least one film-forming polymer may be present in the cosmetic composition in an amount ranging from about 20% to 60% by weight, such as from about 25% to about 50% by weight, or from about 30% to about 40% by weight, relative to the total weight of the cosmetic composition, including all ranges and subranges therebetween. In other embodiments, the at least one film-forming polymer may be present in an amount greater than or equal to about 30% by weight, such as greater than or equal to about 40% by weight, or greater than or equal to about 50% by weight, relative to the total weight of the cosmetic composition.

Silicone Elastomer Blends

As described herein, the cosmetic compositions comprising at least one film-forming polymer further comprise at least one silicone elastomer blend. Silicone elastomer blends useful according to various embodiments of the disclosure may comprise at least one silicone cross-polymer dispersed in at least one oil.

The at least one silicone cross-polymer may, in certain embodiments, be chosen from dimethicone/vinyl dimethicone cross-polymers and dimethicone/phenyl vinyl dimethicone cross-polymers. In other embodiments, the silicone cross-polymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and $C_{30}$-$C_{45}$ alkyl cetearyl dimethicone cross-polymers. Non-limiting examples of polyether modified silicone cross-polymers include dimethicone/PEG-10/15 cross-polymers. Suitable alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

The silicone cross-polymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, e.g., octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, e.g., cetyl dimethicone and lauryl trimethicone; aryl derivatives of linear organopolysiloxanes, e.g., phenyl trimethicone; and hydroxylated derivatives of linear organopolysiloxanes, e.g., dimethiconol. In other embodiments, the oil may be chosen from organic oils, such as mineral oil; linear and branched alkanes, e.g., isododecane; triethylhexanoin; and squalane.

The at least one silicone cross-polymer may, in one embodiment, comprise from about 5% to about 35% by weight, relative to the total weight of the silicone elastomer blend, for example, from about 10% to about 20% by weight, or from about 25% to about 35% by weight, or from about 20% to about 30% by weight, including all ranges and subranges therebetween. The at least one oil may comprise from about 65% to about 95% by weight, relative to the total weight of the silicone elastomer blend, such as from about 80% to about 90% by weight, or from about 65% to about 75% by weight, or from about 70% to about 80% by weight, including all ranges and subranges therebetween.

According to one embodiment, the silicone elastomer blend comprises from about 20% to about 30% of dimethicone/vinyl dimethicone cross-polymer. In another embodiment, the silicone elastomer blend comprises from about 70% to about 80% by weight dimethicone. According to a further embodiment, the silicone elastomer blend comprises from about 20% to about 30% of dimethicone/vinyl dimethicone cross-polymer and from about 70% to about 80% by weight dimethicone.

Non-limiting examples of commercially available silicone elastomer blends include the products sold under the KSG product line by Shin-Etsu, such as KSG-15, KSG-16, and KSG-18, and the products sold under the VELVESIL product line by Momentive, such as VELVESIL 125 and VELVESIL DM.

The at least one silicone elastomer blend may be present in the cosmetic composition in an amount greater than or equal to about 2% by weight, relative to the total weight of the composition. In certain embodiments, the at least one silicone elastomer blend may be present in the cosmetic composition in an amount ranging from about 2% to about 20% by weight, such as from about 2% to about 16% by weight, from about 2% to about 10% by weight, from about 3% to about 8% by weight, or from about 4% to about 6% by weight, relative to the total weight of the cosmetic composition, including all ranges and subranges therebetween. In other embodiments, the at least one silicone elastomer blend may be present in an amount greater than about 2.5% by weight, such as greater than about 3% by weight, greater than about 4% by weight, or greater than about 5% by weight, relative to the total weight of the cosmetic composition.

Waxes

The cosmetic compositions disclosed herein further comprise at least one wax. A "wax" as defined herein is a generally lipophilic compound that is solid at room temperature (25° C.), with a solid/liquid reversible change of state, having a melting point of greater than or equal to 30° C., which may be up to 120° C.

By bringing the wax into a liquid state (melting), it is possible to make it miscible with oils and to form a microscopically uniform mixture, but on cooling the mixture to room temperature, recrystallization of the wax in the oils of the mixture is obtained. For example, the waxes that may be used herein may have a melting point of greater than 45° C., such as greater than or equal to 50° C., or greater than or equal to 55° C. The melting point of the wax may be measured using known methods in the art, for instance, by using a differential scanning calorimeter (DSC).

The waxes that may be used in the cosmetic compositions disclosed herein are chosen from waxes that are solid and rigid at room temperature, of animal, plant, mineral or synthetic origin, and mixtures thereof. The wax may also have a hardness ranging, for example, from 0.05 MPa to 30 MPa, such as from 6 MPa to 15 MPa. The hardness may be determined using known methods in the art, for example, by measuring the compressive strength at 20° C. using a texturometer.

Non-limiting examples of waxes that may be used in compositions of the instant disclosure include hydrocarbon-based waxes such as beeswax, lanolin wax and Chinese insect waxes; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and esters thereof. Silicone waxes and fluoro waxes may also be used.

Waxes obtained by catalytic hydrogenation of animal or plant oils comprising linear or branched $C_8$-$C_{32}$ fatty chains are also suitable for use in the compositions of the disclosure. Among these oils, mention may be made, for example, of hydrogenated jojoba oil, isomerized jojoba oil such as the trans-isomerized partially hydrogenated jojoba oil manufactured or sold by the company Desert Whale under the trade name "Iso-Jojoba-50®", hydrogenated sunflower oil, hydrogenated castor oil, hydrogenated coconut oil and hydrogenated lanolin oil, bis(1,1,1-trimethylolpropane) tetrastearate sold under the name "Hest 2T-4S" by the company Heterene, and bis(1,1,1-trimethylolpropane) tetrabehenate sold under the name "Hest 2T-4B" by the company Heterene.

Further non-limiting examples of suitable waxes include the wax obtained by hydrogenation of olive oil esterified with stearyl alcohol, sold under the name "Phytowax Olive 18 L 57", or the waxes obtained by hydrogenation of castor oil esterified with cetyl alcohol, sold under the name "Phytowax Ricin 16L64 and 22L73" by the company Sophim, may also be used. Such waxes are described in French Patent Application No. 2 792 190, incorporated herein by reference in its entirety.

In one embodiment, the cosmetic composition disclosed herein may comprise at least one "tacky" wax, i.e., a wax with a tack of greater than or equal to 0.7 N·s and a hardness of less than or equal to 3.5 MPa. Using a tacky wax may, for example, make it possible to obtain a cosmetic composition that applies easily to keratin fibers, attaches well to the keratin fibers and leads to the formation of a smooth, uniform and thickening makeup result. The tacky wax used may, for example, have a tack ranging from 0.7 N·s to 30 N·s, such as greater than or equal to 1 N·s, for example, from 1 N·s to 20 N·s, further such as greater than or equal to 2 N·s, for example, from 2 N·s to 10 N·s and further, for example, from 2 N·s to 5 N·s. The tack of the wax may be determined by methods known in the art, for example, by measuring the change in force (compression force or stretching force) as a function of time at 20° C., using a texturometer.

The tacky wax that may be used generally has, for example, a hardness of less than or equal to 3.5 MPa, such as from 0.01 MPa to 3.5 MPa, from 0.05 MPa to 3 MPa, or from 0.1 MPa to 2.5 MPa. The hardness may be measured as described above.

Tacky waxes that may be used include $C_{20}$-$C_{40}$ alkyl (hydroxystearyloxy)stearates (wherein the alkyl group comprises from 20 to 40 carbon atoms), alone or as a mixture, such as a $C_{20}$-$C_{40}$ alkyl 12-(12'-hydroxystearyloxy)stearate, of the following formula:

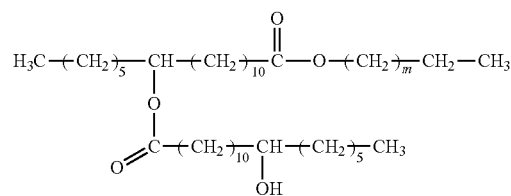

wherein m is an integer ranging from 18 to 38, or a mixture of compounds thereof. Such a wax is, for example, sold under the names "Kester Wax K 82 P®" and "Kester Wax K 80 P®" by the company Koster Keenan.

As disclosed herein, it is also possible to use waxes supplied in the form of small particles having a size, expressed as the mean "effective" volume diameter D[4,3], ranging, for example, from 0.5 to 30 micrometers, such as from 1 to 20 micrometers, further such as from 5 to 10 micrometers in size, which are used herein as "microwaxes."

Among the microwaxes that may be used in the cosmetic compositions as disclosed herein, mention may be made, for example, of carnauba microwaxes, such as the product sold under the name "MicroCare 350®" by the company Micro Powders, synthetic microwaxes, such as the product sold under the name "MicroEase 114S®" by the company Micro Powders, microwaxes comprising a mixture of carnauba wax and polyethylene wax, such as the products sold under the name "Micro Care 300®" and "Micro Care 310®" by the company Micro Powders, microwaxes comprising a mixture of carnauba wax and synthetic wax, such as the product sold under the name "Micro Powders 325®" by the company Micro Powders, polyethylene microwaxes, such as the products sold under the names "Micropoly 200®", "Micropoly 220®", "Micropoly 220L®", and "Micropoly 250S®" by the company Micro Powders, and polytetrafluoroethylene micropowders, such as the products sold under the names "Microslip 519®" and "Microslip 519®" by the company Micro Powders.

The waxes (including the tacky wax) may be present in the form of an aqueous microdispersion of wax. The term "aqueous microdispersion of wax" means an aqueous dispersion of wax particles in which the size of the wax particles is less than or equal to 1 μm. The particles of the wax microdispersion may have, for example, mean sizes of less than 1 μm (such as ranging from 0.02 μm to 0.99 μm) and, for example, less than or equal to 0.5 μm (such as ranging from 0.06 μm to 0.5 μm). The mean "effective" volume diameter D[4,3] as defined above, may be, for example, less than or equal to 1 μm such as less than or equal to 0.75 μm.

These particles consist essentially of a wax or a mixture of waxes. However, they may comprise a small proportion of oily and/or pasty fatty additives, a surfactant and/or a common liposoluble additive/active agent. The wax particles may have varied shapes, for example, they may be spherical.

The cosmetic composition as disclosed herein may comprise a total wax content of greater than or equal to 4% by weight, relative to the total weight of the composition. For example, the at least one wax may be present in the composition in an amount ranging from about 4% to about 40% by weight, such as from about 5% to about 20% by weight, from about 10% to about 35% by weight, or from about 15% to about 30% by weight, relative to the total weight of the composition, including all ranges and subranges therebetween.

Cosmetically Acceptable Medium

The cosmetic composition according to the present invention may comprise a cosmetically acceptable medium such as an aqueous or aqueous-alcoholic medium. The cosmetically acceptable medium may, in certain embodiments, comprise water. The amount of water may be present in an amount ranging from about 15% to about 50% by weight, for example, from about 20% to about 40% by weight, or from about 25% to about 35% by weight, relative to the total weight of the composition, including all ranges and subranges therebetween. The amount of water mentioned above includes the total amount of water present in the aqueous phase, for example, inclusive of the water contributed when at least one film-forming polymer is present in the form of dispersed particles.

The aqueous medium may further comprise at least one organic solvent. In certain embodiments, the organic solvent is water-miscible. Non-limiting examples of suitable organic solvents include $C_1$-$C_4$ alkanols, such as ethanol and isopropanol; glycerol; glycols and glycol ethers such as 2-butoxyethanol, propylene glycol, monomethyl ether of propylene glycol, monoethyl ether and monomethyl ether of diethylene glycol; and aromatic alcohols such as benzyl alcohol and phenoxyethanol; analogous products; and mixtures thereof. The organic solvents may be present in an amount ranging from about 1% to about 40% by weight, for example, from about 1% to about 30% by weight, or from about 5% to about 20% by weight, relative to the total weight of the composition, including all ranges and subranges therebetween.

Oils

The cosmetic compositions disclosed herein may also comprise at least one oil. The at least one oil may, for example, be chosen from volatile oils and non-volatile oils, and mixtures thereof. In at least one embodiment, the cosmetic composition of the instant disclosure comprises at least one volatile oil.

As used herein, the term "volatile oil" means an oil that is capable of evaporating on contact with the skin or a keratin fiber in less than one hour, at room temperature and atmospheric pressure. The at least one volatile organic solvent and the at least one volatile oil disclosed herein are volatile organic solvents and cosmetic oils that are liquid at room temperature, with a non-zero vapor pressure at room temperature and atmospheric pressure, ranging, for example, from 0.13 Pa to 40,000 Pa ($10^{-3}$ to 300 mmHg), such as from 1.3 Pa to 13,000 Pa (0.01 to 100 mmHg), or from 1.3 Pa to 1,300 Pa (0.01 to 10 mmHg). The term "non-volatile oil" means an oil that remains on the skin or the keratin fiber at room temperature and atmospheric pressure for at least several hours and that has, for example, a vapor pressure of less than $10^{-3}$ mmHg (0.13 Pa).

The volatile oils may be chosen, for example, from hydrocarbon-based oils, silicone oils, fluoro oils, and mixtures thereof.

As used herein, the term "hydrocarbon-based oil" means an oil mainly comprising hydrogen and carbon atoms and optionally oxygen, nitrogen, sulfur and/or phosphorus atoms. The volatile hydrocarbon-based oils may be chosen, for example, from hydrocarbon-based oils comprising from 8 to 16 carbon atoms, such as branched $C_8$-$C_{16}$ alkanes, for instance $C_8$-$C_{16}$ isoalkanes of petroleum origin (also known as isoparaffins), such as isododecane (also known as 2,2,4,4,6-pentamethylheptane), isodecane and isohexadecane, for example, the oils sold under the trade names Isopar or Permethyl, branched $C_8$-$C_{16}$ esters and isohexyl neopentanoate, and mixtures thereof. Other volatile hydrocarbon-based oils, for instance petroleum distillates, such as those sold under the name Shell Solt by the company Shell, may also be used. The volatile solvent may be chosen, for example, from volatile hydrocarbon-based oils comprising from 8 to 16 carbon atoms, and mixtures thereof.

The volatile oils that may also be used include, for example, volatile silicones, for instance volatile linear or cyclic silicone oils, such as those with a viscosity ≤8 centistokes ($8 \times 10^{-5}$ m$^2$/s) and, for example, comprising from 2 to 7 silicon atoms, these silicones optionally comprising at least one group chosen from alkyl and alkoxy groups comprising from 1 to 10 carbon atoms. Among the volatile silicone oils that may be used herein, mention may be made, for example, of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

Volatile fluorinated solvents such as nonafluoromethoxybutane or perfluoromethylcyclopentane may, for example, also be used.

The volatile oil may be present in the cosmetic composition in an amount ranging, for example, from about 0.1% to about 60% by weight, such as from about 0.1% to about 30% by weight, relative to the total weight of the composition, including all ranges and subranges therebetween.

The cosmetic composition may also comprise at least one non-volatile oil chosen, for example, from non-volatile hydrocarbon-based oils, silicone oils, and fluoro oils.

Non-volatile hydrocarbon-based oils that may be mentioned include, for example:

hydrocarbon-based oils of plant origin, such as triglycerides comprising fatty acid esters of glycerol, the fatty acids of which may have varied chain lengths from $C_4$ to $C_{24}$, these chains possibly being linear or branched, and saturated or unsaturated; these oils are chosen, for example, from wheatgerm oil, sunflower oil, grapeseed oil, sesame seed oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel, synthetic ethers comprising from 10 to 40 carbon atoms;

linear or branched hydrocarbons of mineral or synthetic origin, such as petroleum jelly, polydecenes, hydrogenated polyisobutene such as parleam, squalane, and mixtures thereof;

synthetic esters such as oils of formula $R_1COOR_2$ wherein $R_1$ is chosen from linear and branched fatty acid residues comprising from 1 to 40 carbon atoms and $R_2$ is chosen from branched hydrocarbon-based chains comprising from 1 to 40 carbon atoms, provided that the number of carbon atoms is $R_1+R_2 \geq 10$, such as, purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, comprising a branched and/or unsaturated carbon-based chain comprising from 12 to 26 carbon atoms, for instance octyldodecanol, isostearyl alcohol, oleyl alcohol, 2-hexyldecanol, 2-butyloctanol and 2-undecylpentadecanol;

higher fatty acids such as oleic acid, linoleic acid and linolenic acid; and mixtures thereof.

The non-volatile silicone oils that may be used include, for example, non-volatile polydimethylsiloxanes (PDMSs), polydimethylsiloxanes comprising alkyl or alkoxy groups, that are pendent and/or at the end of a silicone chain, wherein the alkyl or alkoxy groups each comprise from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Non-limiting examples of fluoro oils that may be used herein include fluorosilicone oils, fluoropolyethers, and fluorosilicones, for example, those described in European Patent Application No. 0 847 752.

The non-volatile oils may be present in the cosmetic composition as disclosed herein in an amount ranging, for example, from about 0.1% to about 20% by weight, such as from about 0.1% to about 12% by weight, relative to the total weight of the composition, including all ranges and subranges therebetween.

Dyestuffs

As disclosed herein, the cosmetic composition may optionally comprise at least one dyestuff. Suitable dyestuffs include but are not limited to pulverulent dyestuffs, liposoluble dyes, and water-soluble dyes. The at least one dyestuff may be present in the cosmetic composition in an amount ranging from about 0.01% to about 30% by weight of the total weight of the composition, including all ranges and subranges therebetween.

The pulverulent dyestuffs may, for instance, be chosen from pigments and nacres.

The pigments, which may be used according to the present disclosure, may, in certain embodiments, be chosen from white, colored, inorganic, organic, polymeric, nonpolymeric, coated and uncoated pigments. Representative examples of inorganic pigments include titanium dioxide, optionally surface-treated, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

The nacres which may be used according to the present invention may be chosen, for example, from white nacreous pigments such as mica coated with titanium or with bismuth oxychloride, colored nacreous pigments such as titanium mica with iron oxides, titanium mica with iron oxides, titanium mica with ferric blue or chromium oxide, titanium mica with an organic pigment chosen from those mentioned above, and nacreous pigments based on bismuth oxychloride.

Representative liposoluble dyes which may be used according to the present disclosure include Sudan Red, DC Red 17, DC Green 6, β-carotene, soybean oil, Sudan Brown, DC Yellow 11, DC Violet 2, DC Orange 5, annatto, and quinoline yellow.

The water-soluble dyes which may be used according to the present invention include, but are not limited to, beetroot juice, methylene blue, the disodium salt of ponceau, the disodium salt of alizarin green, quinoline yellow, the trisodium salt of amaranth, the disodium salt of tartrazine, the monosodium salt of rhodamine, the disodium salt of fuchsin, and xanthophyll.

Fillers

The cosmetic composition disclosed herein may also comprise at least one filler commonly used in the art in cosmetic compositions. The fillers may be lamellar or non-lamellar, inorganic or organic particles. Representative examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance Teflon®, lauroyllysine, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example, Tospearls® from Toshiba), precipitated calcium carbonate, magnesium carbonate, magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, preferably from 12 to 18 carbon atoms, for example, zinc stearate, magnesium stearate, lithium stearate, zinc laurate, or magnesium myristate.

The fillers, if present, are present in amounts generally ranging from about 0.1% to about 25%, such as from about 1% to about 20% by weight, relative to the total weight of the composition, including all ranges and subranges therebetween.

Fibers

In some embodiments, the cosmetic composition may further comprise at least one fiber, which may improve the lengthening effect of the composition. The fibers useful in the present disclosure may be chosen from rigid or non-rigid fibers and may be of natural or synthetic origin. Natural fibers include, but are not limited to, cotton, silk, wool, and other keratin fibers. Synthetic fibers include, but are not limited to, polyester, rayon, nylon, and other polyamide fibers. In some embodiments, fibers may be made of non-rigid fibers such as polyamide (Nylon®) fibers, or rigid fibers such as polyimideamide fibers, for instance, those sold under the trade name "Kermel" and "Kermel Tech" by Rhodia, or poly(p-phenyleneterephthalamide) (or aramid) fibers sold especially under the name Kevlar® by DuPont de Nemours.

The fibers, if present, may be present in the cosmetic composition in an amount generally ranging from about 0.01% to about 10% by weight, relative to the total weight of the composition, including all ranges and subranges therebetween, including all ranges and subranges therebetween.

Surfactants

The cosmetic composition according to the disclosure may further comprise at least one surfactant. For example, the composition may comprise at least one surfactant chosen from cationic, anionic, non-ionic and zwitterionic surfactants. The at least one surfactant may generally be present in a total amount ranging from about 0.01% to about 50% by weight, for example, from about 1% to about 30% by weight, or from about 2% to about 10% by weight, relative to the total weight of the cosmetic composition, including all ranges and subranges therebetween.

In certain embodiments, the cosmetic composition may comprise at least one anionic surfactant. Suitable anionic surfactants may include, but are not limited to, fatty acids such as $C_{16}$-$C_{24}$ fatty acids and combinations thereof. As used herein, the term "fatty acid" means a carboxylic acid with a long aliphatic carbon chain. The fatty acid may be chosen from any saturated or unsaturated, linear or branched fatty acids, for instance, palmitic acid, margaric acid, stearic acid, nonadecylic acid, arachidic acid, heneicosylic acid, behenic acid, tricosylic acid, lignoceric acid, and mixtures thereof.

Other suitable anionic surfactants include, by way of non-limiting example:
  polyoxyethylenated fatty acid salts, for example, those derived from amines or alkali metal salts, and mixtures thereof;
  phosphoric esters and salts thereof, such as "DEA oleth-10 phosphate" ("Crodafos N 10N" from the company Croda);
  sulfosuccinates such as "Disodium PEG-5 citrate lauryl sulfosuccinate" and "Disodium ricinoleamido MEA sulfosuccinte";
  alkyl ether sulfates, such as sodium lauryl ether sulfate;
  isethionates;
  acylglutamate such as "Disodium hydrogenated tallow glutamate" ("Amisoft HS-21 R" sold by the company Ajinomoto);
  2-amino-2-methyl-1,3-propanediol (AMPD); and mixtures thereof.

The anionic surfactant may be present in the cosmetic composition in an amount ranging from about 0.01% to about 10% by weight, for instance, from about 0.1% to about 5% by weight, and more preferably about 0.5 to about 3% by weight, relative to the total weight of the cosmetic composition, including all ranges and subranges therebetween.

According to other embodiments, the cosmetic composition may comprise at least one non-ionic surfactant. For instance, the non-ionic surfactant may have an HLB of less than 8 at 25° C. or an HLB of greater than 8 at 25° C.

As non-limiting examples of nonionic surfactants with an HLB of less than 8 at 25° C., mention may be made of:
  saccharide esters and ethers, such as sucrose stearate, sucrose cocoate, sorbitan stearate, and mixtures thereof, for instance "Arlatone 2121" sold by the company ICI;
  fatty acid esters (especially of a $C_8$-$C_{24}$ acid and preferably a $C_{16}$-$C_{22}$ acid) of polyol, especially of glycerol or of sorbitol, for instance, glyceryl stearate such as the product sold under the name "Tegin M" by the company Goldschmidt; glyceryl laurate such as the product sold under the name "Imwitor 312" by the company Hüls; polyglyceryl-2 stearate, sorbitan tristearate or glyceryl ricinoleate; and
  a mixture of cyclomethicone/dimethicone copolyol sold under the name "Q2-3225C" by the company Dow Corning.

By way of non-limiting example, the nonionic surfactant with an HLB of less than 8 at 25° C. may be present in the composition in an amount ranging from about 0.01% to about 40% by weight, for instance, from about 0.1% to about 25% by weight, from about 0.2% to about 15% by weight, or from about 0.4% to about 10% by weight, relative to the total weight of the composition, including all ranges and subranges therebetween.

Nonionic surfactants with an HLB of greater than 8 at 25° C., may include, but are not limited to:
  oxyethylenated and/or oxypropylenated ethers (which may comprise from 1 to 150 oxyethylene and/or oxypropylene groups) of glycerol;
  oxyethylenated and/or oxypropylenated ethers (which may comprise from 1 to 150 oxyethylene and/or oxypropylene groups) of fatty alcohols (for instance of a $C_8$-$C_{24}$ alcohol or of a $C_{12}$-$C_{18}$ alcohol), such as oxyethylenated cetearyl alcohol ether containing 30 oxyethylene groups (CTFA name "Ceteareth-30"), oxyethylenated stearyl alcohol ether containing 20 oxyethylene groups (CTFA name "Steareth-20"), and the oxyethylenated ether of the mixture of $C_{12}$-$C_{15}$ fatty alcohols comprising 7 oxyethylene groups (CTFA name "$C_{12-15}$ Pareth-7" sold under the name "Neodol 25-7®" by Shell Chemicals);
  fatty acid esters (for example of a $C_8$-$C_{24}$ acid or of a $C_{16}$-$C_{22}$ acid) of polyethylene glycol (which may comprise from 1 to 150 ethylene glycol units), such as PEG-50 stearate and PEG-40 monostearate sold under the name "Myrj 52P" by the company ICI Uniqema;
  fatty acid esters (for instance of a $C_8$-$C_{24}$ acid or of a $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name "Simulsol 200 TM" by the company SEPPIC; glyceryl stearate polyethoxylated with 30 ethylene oxide groups, for instance the product "Tagat S" sold under the company Goldschmidt; glyceryl oleate polyethoxylated with 30 ethylene oxide groups, for instance the product "Tagat O" sold by the company Goldschmidt; glyceryl cocoate polyethoxylated with 30 ethylene oxide groups, for instance the product "Varionic LI 13" sold by the company Sherex; glyceryl isostearate polyethoxylated with 30 ethylene oxide groups, for instance the product "Tagat L" sold by the company Goldschmidt; and glyceryl laurate polyethoxylated with 30 ethylene oxide groups, for instance the product "Tagat I" form the company Goldschmidt;
  fatty acid esters (for example of a $C_8$-$C_{24}$ acid or of a $C_{16}$-$C_{22}$ acid) of oxyethylenated and/or oxypropylenated sorbitol ethers (which may comprise from 1 to 150 oxyethylene and/or oxypropylene groups), for instance polysorbate 60 sold under the name "Tween 60" by the company Uniqema;
  dimethicone copolyol, such as the product sold under the name "Q2-5220" by the company Dow Corning;
  dimethicone copolyol benzoate (Finsolv SLB 101 and 201 by the company Finetex);
  copolymers of propylene oxide and of ethylene oxide, also known as EO/PO polycondensates; and
  mixtures thereof.

The EO/PO polycondensates may be chosen from those comprising polyethylene glycol and polypropylene glycol blocks, for instance polyethylene glycol/polypropylene glycol/polyethylene glycol triblock polycondensates. These triblock polycondensates may have, for example, the following chemical structure:

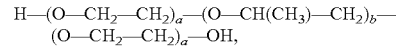

in which a ranges from 2 to 120 and b ranges from 1 to 100.

The EO/PO polycondensate may, in certain embodiments, have a weight-average molecular weight ranging from about 1,000 to about 15,000, for example, from 2,000 to 13,000. In other embodiments, the EO/PO polycondensate may have a cloud point, at 10 g/l in distilled water, of greater than or equal to 20° C., for instance, greater than or equal to 60° C. The cloud point is measured according to ISO standard 1065. As EO/PO polycondensates that may be used according to the invention, mention may be made of the polyethylene glycol/polypropylene glycol/polyethylene glycol triblock polycondensates sold under the name "Synperonic", for instance "Synperonic PE/L44" and "Synperonic PE/F127", by the company ICI, and mixtures thereof.

By way of non-limiting example, the nonionic surfactant with an HLB of greater than 8 at 25° C. may be present in the composition in an amount ranging from about 0.01% to about 40% by weight, for instance, from about 0.1% to about 25% by weight, from about 0.2% to about 15% by weight, or from about 0.4% to about 10% by weight, relative to the total weight of the composition, including all ranges and subranges therebetween.

Additives

The cosmetic composition of the invention may also comprise at least one additive conventionally used in the cosmetic art. For example, the composition may include dispersants, antioxidants, essential oils, sunscreens, preserving agents, fragrances, neutralizing agents, cosmetic and dermatological active agents such as, for example, emollients, moisturizers, vitamins, essential fatty acids, surfactants, pasty compounds, and mixtures thereof. A non-exhaustive listing of such ingredients can be found in U.S. Patent Application Publication No. 2004/0170586, incorporated herein by reference in its entirety. Still further examples of such additional ingredients may be found in the International Cosmetic Ingredient Dictionary and Handbook (9th edition, 2002).

In certain embodiments, the cosmetic composition is free of soaps, such as triethanolamine (TEA)-stearate and 2-amino-2-methyl-1-propanol (AMP)-stearate. It is believed that such compounds may serve as plasticizers, which prevent the lifting up of the eyelashes and/or cause smudging around the eyes when users attempt to remove the cosmetic composition using only warm water.

One of skill in the art will take care to select the optional additional additives and/or the amount thereof such that the advantageous properties of the cosmetic composition according to the invention are not, or are not substantially, adversely affected by the envisaged addition. The types and amounts of these additives may be selected based on, for example, the type of cosmetic composition being formulated and the desired properties thereof.

These additives may generally be present in the cosmetic composition in an amount ranging from about 0% to about 90%, for example, from about 0.01% to 80%, or from about 0.1% to about 50% by weight, relative to the total weight of the composition, including all ranges and subranges therebetween.

Needless to say, the cosmetic composition of the invention should be cosmetically and/or dermatologically acceptable, i.e., it should contain a non-toxic physiologically acceptable medium and should be able to be applied to the keratinous materials of human beings. Exemplary cosmetic compositions contemplated according to the disclosure include compositions intended for application to keratinous fibers, such as the eyelashes. Such compositions include, but are not limited to, mascara compositions.

Without wishing to be bound by theory, it is believed that the incorporation of at least one silicone elastomer blend, in the amounts disclosed herein, may serve to thicken the cosmetic composition, while also dispersing the particulate components, such as film-forming polymers, pigments, waxes, and the like. Thus, compositions of the instant disclosure may unexpectedly serve to both lengthen and thicken the eyelashes while also avoiding clumping of the composition on the eyelashes and/or sticking together of the eyelashes.

By way of example only, the mascara formulations described herein have been found to have improved thickening and volumizing properties, while also lengthening the eyelashes with satisfactory lash separation and resistance to clumping. It should be noted, however, that compositions according to the disclosure may not have one or more of the above-referenced improved properties, yet such compositions are intended to be within the scope of the disclosure.

Cosmetic Method

The instant disclosure also relates to a cosmetic method for making up and/or enhancing the appearance of a keratinous substrate, the method comprising applying to the keratinous substrate a composition comprising (1) at least one film-forming polymer, present in an amount greater than or equal to about 20% by weight, relative to the total weight of the composition, (2) at least one silicone elastomer blend comprising at least one silicone cross-polymer dispersed in at least one oil, present in an amount greater than or equal to about 2% by weight, relative to the total weight of the composition, and (3) at least one wax, present in an amount greater than or equal to about 4% by weight, relative to the total weight of the composition. All embodiments disclosed above with respect to the cosmetic composition are equally applicable to the cosmetic method and are intended to fall within the scope of the disclosure.

According to one embodiment of the present disclosure, a cosmetic process for making up eyelashes is provided. This process may, in certain embodiments, comprise the steps of loading an applicator with a cosmetic composition disclosed herein, and applying said cosmetic composition onto the eyelashes. In certain embodiments, the cosmetic composition may be applied to the eyelashes more than once, such as twice or three or more times, according to the cosmetic effect desired by the user.

The cosmetic composition according to the invention may be packed in a cosmetic container delimiting at least one compartment which comprises the cosmetic composition, the container being closed by a closing member.

The container is, according to various embodiments, combined with an applicator, such as a brush comprising an arrangement of bristles maintained by a twisted wire. Such a twisted brush is described, for example, in U.S. Pat. No. 4,887,622, incorporated herein by reference in its entirety. The applicator may also be in the form of a comb comprising a plurality of application members, which may be obtained by moulding. Such combs are described, for example, in French Patent No. 2 796 529, incorporated herein by reference in its entirety. The applicator may be integrally attached to the container, as described for example in French Patent No. 2 761 959. In other embodiments, the applicator is integrally attached to a rod which is itself integrally attached to the closing member.

The closing member may be coupled to the container by screwing. Alternatively, the coupling between the closing member and the container is achieved by a method other than by screwing, such as via a bayonet mechanism, by click-fastening or by tightening. The container may be at least partially made of thermoplastic material. Examples of thermoplastic materials that may be mentioned include polypropylene or polyethylene. Alternatively, the container may be made of non thermoplastic material, such as glass or metal (or alloy).

In some embodiments, the container may also be equipped with a drainer arranged in the region of the aperture of the container. Such a drainer makes it possible to wipe the applicator and possibly the rod to which it may be integrally attached. Such a drainer is described, for example, in French Patent No. 2 792 618.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a film-forming polymer" is intended to mean at least one film-forming polymer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Inventive Example A and Comparative Example B

Mascara Compositions

Two mascara compositions were prepared by mixing, independently, the components set forth in the following Table 1 and Table 2.

TABLE 1

| INVENTIVE COMPOSITION A | |
|---|---|
| Component | Wt % |
| Waxes | 14.8 |
| Anionic Surfactants | 2.05 |
| Non-ionic Surfactants | 3.0 |
| Water | 25.9 |
| Alcohol | 0.5 |
| Pigment | 7 |
| Thickener | 0.6 |
| Silicone Elastomer Blend | 2 |
| Silicone | 1 |
| Film-forming Polymer (39.34% A.M.) | 40 |

TABLE 1-continued

| INVENTIVE COMPOSITION A | |
|---|---|
| Component | Wt % |
| Silicone/Plasticizer | 0.25 |
| Preservative | 0.5 |
| Co-preservatives | 0.4 |
| Alcohol Denat. | 2 |

TABLE 2

| COMPARATIVE COMPOSITION B | |
|---|---|
| Component | Wt % |
| Waxes | 11.0 |
| Anionic Surfactants | 2.05 |
| Non-ionic Surfactants | 3.0 |
| Water | 27.53 |
| Alcohol | 0.5 |
| Pigment | 5 |
| Thickener | 0.9 |
| Film-forming Polymer (39% A.M.) | 40 |
| Film-forming Polymer (100% A.M.) | 2 |
| Preservatives | 0.36 |
| Co-preservatives | 0.3 |
| Glycols | 4.35 |
| Fibers | 3.01 |

Model Evaluation Test 1

Method

Inventive composition A and comparative composition B were subjected to sensory evaluation tests with regard to various cosmetic properties by 12 testers. The panel consisted of women, ages 19-49, who use non-waterproof black brush mascara more than five days a week and who expect a thickening effect and clean finish from their mascara. Inventive composition A and comparative composition B were used in the women's usual home makeup routine for a week, with composition A being used for 5 days and composition B being used for 2 days.

Monadic Evaluation

The panel was asked to evaluate inventive composition A on its own, without comparison to any other product. The results of this evaluation are illustrated in the following Table 3, in which "+" indicates that a majority of users found that inventive composition A satisfactorily achieved the evaluated property, "−" indicates that a majority of users found that inventive composition A did not satisfactorily achieve the evaluated property, and "≈" indicates that the evaluations of the property were mixed.

TABLE 3

| MONADIC TEST 1 RESULTS | |
|---|---|
| PROPERTY | RATING |
| Application | |
| Sufficient amount deposited with one coat | + |
| Ease of application | + |
| Good texture/reduced or no clumping | ≈ |
| Dried fast | ≈ |
| Did not impart a dragging feel | ≈ |
| Did not stick the lashes together | − |
| Sensation | |
| No discomfort | + |

TABLE 3-continued

MONADIC TEST 1 RESULTS

| PROPERTY | RATING |
|---|---|
| Makeup Result | |
| Thickened the lashes | + |
| Lengthened the lashes | + |
| Clean finish-reduced or no clumping | ≈ |
| Clean finish-lash separation | ≈ |
| Fixed curls created by lash curler | ≈ |
| Daytime Wear | |
| No smudging | + |
| No weighing down of lashes | + |
| No flaking | + |
| Removal | |
| Easy to remove | ≈ |

As demonstrated by Table 3 above, inventive composition A exhibited not only a favorable thickening effect and one-coat application, but also a favorable lengthening effect, as well as other favorable properties such as smudge and flake resistance, ease of application, and lack of discomfort during wear.

Comparative Evaluation

The panel was asked to evaluate composition as compared to composition B (not comprising a silicone elastomer blend). The results of this testing are illustrated in the following Table 4, in which "○○○" indicates that a majority of users found that inventive composition A outperformed comparative composition B with respect to the evaluated property, "○" indicates that a majority of users found that comparative composition B outperformed inventive composition A with respect to the evaluated property, and "○○" indicates that compositions A and B performed roughly equally.

TABLE 4

COMPARATIVE TEST 1 RESULTS

| PROPERTY | RATING |
|---|---|
| Application | |
| Sufficient amount deposited with one coat | ○○○ |
| Buildable volume | ○○○ |
| Dried fast | ○ |
| Did not impart a dragging feel | ○ |
| Makeup Result | |
| Thickened the lashes | ○○○ |
| Lengthened the lashes | ○○ |
| Clean finish-reduced or no clumping | ○ |
| Clean finish-lash separation | ○ |

As demonstrated by Table 4 above, inventive composition A exhibited not only an improved thickening effect and enhanced one-coat application, but also demonstrated a lengthening effect comparable to that of composition B. Thus, inventive composition A achieves the goal of simultaneously thickening and lengthening the lashes, and is unexpectedly superior to composition B (not comprising a silicone elastomer blend) with respect to improved ability to thicken the lashes.

Model Evaluation Test 2

Method

Inventive composition A and comparative composition B were subjected to sensory evaluation tests with regard to various cosmetic properties by 12 testers. The panel consisted of women, ages 19-49, who use non-waterproof black brush mascara more than five days a week and who expect a thickening effect and clean finish from their mascara. Inventive composition A and comparative composition B were used in the women's usual home makeup routine for a week in rotated order (each composition used for 3 or 4 days).

Monadic Evaluation

The panel was asked to evaluate inventive composition A on its own, without comparison to any other product. The results of this evaluation are illustrated in the following Table 5, in which "+" indicates that a majority of users found that inventive composition A satisfactorily achieved the evaluated property, "−" indicates that a majority of users found that inventive composition A did not satisfactorily achieve the evaluated property, and "≈" indicates that the evaluations of the property were mixed.

TABLE 5

MONADIC TEST 2 RESULTS

| PROPERTY | RATING |
|---|---|
| Application | |
| Sufficient amount deposited with one coat | + |
| Ease of application | + |
| Good texture/reduced or no clumping | − |
| Dried fast | + |
| Did not impart a dragging feel | ≈ |
| Did not stick the lashes together | ≈ |
| Sensation | |
| No discomfort | + |
| Makeup Result | |
| Thickened the lashes | + |
| Lengthened the lashes | + |
| Clean finish-reduced or no clumping | ≈ |
| Clean finish-lash separation | ≈ |
| Fixed curls created by lash curler | + |
| Daytime Wear | |
| No smudging | + |
| No weighing down of lashes | + |
| No flaking | + |
| Removal | |
| Easy to remove | + |

As demonstrated by Table 5 above, inventive composition A exhibited not only a favorable thickening effect and one-coat application, but also a favorable lengthening effect, as well as other favorable properties such as smudge and flake resistance, ease of application and removal, and lack of discomfort during wear.

Comparative Evaluation

The panel was asked to evaluate composition as compared to composition B (not comprising a silicone elastomer). The results of this testing are illustrated in the following Table 6, in which "○○○" indicates that a majority of users found that inventive composition A outperformed comparative composition B with respect to the evaluated property, "○" indicates that a majority of users found that comparative composition B outperformed inventive composition A with respect to the evaluated property, and "○○" indicates that compositions A and B performed roughly equally.

TABLE 6

COMPARATIVE TEST 2 RESULTS

| PROPERTY | RATING |
| --- | --- |
| Application | |
| Sufficient amount deposited with one coat | ooo |
| Did not impart a dragging feel | o |
| Makeup Result | |
| Thickened the lashes | ooo |
| Lengthened the lashes | o |
| Clean finish-reduced or no clumping | o |
| Clean finish-lash separation | o |
| Daytime Wear | |
| No smudging | oo |
| No weighing down of lashes | o |
| No flaking | oo |
| Removal | |
| Easy to remove | oo |

As shown in Table 6 above, inventive composition A exhibited an improved thickening effect and one-coat application as compared to composition B. Further, Table 5 indicates that inventive composition A exhibits a satisfactory lengthening effect. Thus, inventive composition A achieves the goal of simultaneously thickening and lengthening the lashes, and is unexpectedly superior to composition B (not comprising a silicone elastomer blend) with respect to improved ability to thicken the lashes.

What is claimed is:

1. A mascara composition comprising:
   (a) at least one film-forming polymer, present in an amount greater than or equal to 25% by weight relative to the total weight of the composition;
   (b) at least one silicone elastomer blend comprising at least one silicone cross-polymer dispersed in at least one oil, present in an amount greater than or equal to 2% by weight relative to the total weight of the composition;
   (c) at least one wax, present in an amount greater than or equal to 4% by weight relative to the total weight of the composition; and
   (d) water, present in an amount ranging from about 15% to about 50% by weight relative to the total weight of the composition.

2. The mascara composition of claim 1, wherein the at least one film-forming polymer is chosen from synthetic polymers, of the free-radical type or of the polycondensate type, and polymers of natural origin, and mixtures thereof.

3. The mascara composition of claim 2, wherein the at least one film-forming polymer is chosen from vinyl (co)polymers, (meth)acrylic (co)polymers, urethane (co)polymers, and mixtures thereof.

4. The mascara composition of claim 1, wherein the at least one film-forming polymer is present in the cosmetic composition in an amount ranging from about 25% to about 60% by weight relative to the total weight of the composition.

5. The mascara composition of claim 1, wherein the at least one silicone elastomer blend is at least one silicone cross-polymer dispersed in at least one oil chosen from silicone oils and organic oils.

6. The mascara composition of claim 5, wherein the at least one silicone elastomer blend is dimethicone/vinyl dimethicone cross-polymer dispersed in dimethicone.

7. The mascara composition of claim 1, wherein the at least one silicone elastomer is present in the cosmetic composition in an amount ranging from about 2% to about 20% by weight relative to the total weight of the composition.

8. The mascara composition of claim 1, wherein the at least one wax is chosen from beeswax, lanolin wax, Chinese insect waxes, rice wax, carnauba wax, candelilla wax, ouricury wax, esparto grass wax, cork fibre wax, sugar cane wax, Japan wax, sumach wax, montan wax, microcrystalline waxes, paraffins, ozokerite, polyethylene waxes, waxes obtained by Fisher-Tropsch synthesis, waxy copolymers, silicone waxes, fluoro waxes, tacky waxes, and microwaxes, and esters thereof, and mixtures thereof.

9. The mascara composition of claim 1, wherein the at least one wax is present in the cosmetic composition in an amount ranging from about 4% to about 40% by weight relative to the total weight of the composition.

10. A method for making up and/or enhancing the appearance of a keratinous substrate comprising applying to the keratinous substrate a mascara composition comprising:
    (a) at least one film-forming polymer, present in an amount greater than or equal to 25% by weight relative to the total weight of the composition;
    (b) at least one silicone elastomer blend comprising at least one silicone cross-polymer dispersed in at least one oil, present in an amount greater than or equal to 2% by weight relative to the total weight of the composition;
    (c) at least one wax, present in an amount greater than or equal to 4% by weight relative to the total weight of the composition; and
    (d) water, present in an amount ranging from about 15% to about 50% by weight relative to the total weight of the composition.

11. The method of claim 10, wherein the at least one film-forming polymer is chosen from synthetic polymers, of the free-radical type or of the polycondensate type, and polymers of natural origin, and mixtures thereof.

12. The method of claim 11, wherein the at least one film-forming polymer is chosen from vinyl (co)polymers, (meth)acrylic (co)polymers, urethane (co)polymers, and mixtures thereof.

13. The method of claim 10, wherein the film-forming polymer is present in the cosmetic composition in an amount ranging from about 25% to about 60% by weight relative to the total weight of the composition.

14. The method of claim 10, wherein the at least one silicone elastomer blend is at least one silicone cross-polymer dispersed in at least one oil chosen from silicone oils and organic oils.

15. The method of claim 14, wherein the at least one silicone elastomer blend is dimethicone/vinyl dimethicone cross-polymer dispersed in dimethicone.

16. The method of claim 10, wherein the at least one silicone elastomer blend is present in the cosmetic composition in an amount ranging from about 2% to about 20% by weight relative to the total weight of the composition.

17. The method of claim 10, wherein the at least one wax is chosen from beeswax, lanolin wax, Chinese insect waxes, rice wax, carnauba wax, candelilla wax, ouricury wax, esparto grass wax, cork fibre wax, sugar cane wax, Japan wax, sumach wax, montan wax, microcrystalline waxes, paraffins, ozokerite, polyethylene waxes, waxes obtained by Fisher-Tropsch synthesis, waxy copolymers, silicone waxes, fluoro waxes, tacky waxes, and microwaxes, and esters thereof, and mixtures thereof.

18. The method of claim 10, wherein the at least one wax is present in the cosmetic composition in an amount ranging from about 4% to about 40% by weight relative to the total weight of the composition.

19. The method of claim 10, wherein the keratinous substrate is the eyelashes.

\* \* \* \* \*